US00PP33110P2

(12) United States Plant Patent
Wheeler et al.

(10) Patent No.: US PP33,110 P2
(45) Date of Patent: Jun. 1, 2021

(54) BLUEBERRY PLANT NAMED 'BB07-249GA-3'

(50) Latin Name: *Vaccinium corymbosum*
Varietal Denomination: BB07-249GA-3

(71) Applicant: Berry Blue, LLC, Grand Junction, MI (US)

(72) Inventors: Edmund J. Wheeler, Holland, MI (US); James F. Hancock, Scarborough, ME (US)

(73) Assignee: Berry Blue, LLC, Grand Junction, MI (US)

( * ) Notice: Subject to any disclaimer, the term of this patent is extended or adjusted under 35 U.S.C. 154(b) by 2 days.

(21) Appl. No.: 16/602,948

(22) Filed: Jan. 2, 2020

(51) Int. Cl.
*A01H 5/08* (2018.01)
*A01H 6/36* (2018.01)

(52) U.S. Cl.
USPC ..... Plt./157
CPC ..... *A01H 6/368* (2018.05)

(58) Field of Classification Search
USPC ..... Plt./157
CPC ..... A01H 5/08
See application file for complete search history.

*Primary Examiner* — Kent L Bell
(74) *Attorney, Agent, or Firm* — King IP Law; Joshua King

(57) ABSTRACT

A new and distinct cultivar of blueberry plant named 'BB07-249GA-3' as described and shown herein. 'BB07-249GA-3' is a new and distinct low chill tetraploid Southern highbush blueberry (*Vaccinium*) variety consisting of primarily *V. corymbosum*, with a limited contribution of genes from *V. ashei* and *V. darrowi*. It is a very productive early maturing variety. It is characterized as having large fruit, medium blue in color and is very firm with a very small and dry picking scar. The fruit is well exposed on a vigorous slightly spreading bush.

5 Drawing Sheets

Latin name: *Vaccinium corymbosum.*

BACKGROUND AND SUMMARY

Blueberries are a well-known fruit enjoyed by many throughout the world. One example of an existing, patented blueberry variety is 'Springhigh', U.S. Plant Pat. No. 9,834. Another example of an existing, patented blueberry variety is 'Star', U.S. Plant Pat. No. 10,675.

Compared to 'Springhigh', 'BB07-249GA-3' is more rounded, the leaves are shorter in length and not as wide, the berry weight is greater, the firmness is much greater, the date of 50% ripe fruit is 12 days earlier, and the date of 50% open flowers is 7 days before 'Springhigh'. The leaf margins are entire while for 'Springhigh' the leaf margins are serrated.

Compared to 'Star', 'BB07-249GA-3' is more spreading, the berry size and weight are greater, the leaves are much longer and narrower, the berry firmness is greater, the Brix° level is much greater, the date of 50% ripe fruit is 21 days earlier and the date of 50% open flowers is 10 days earlier.

The present cultivar, 'BB07-249GA-3', provides one or more advantages compared to these and/or other blueberry varieties.

BRIEF DESCRIPTION OF THE PHOTOGRAPHS

DETAILED DESCRIPTION

Figure 1:
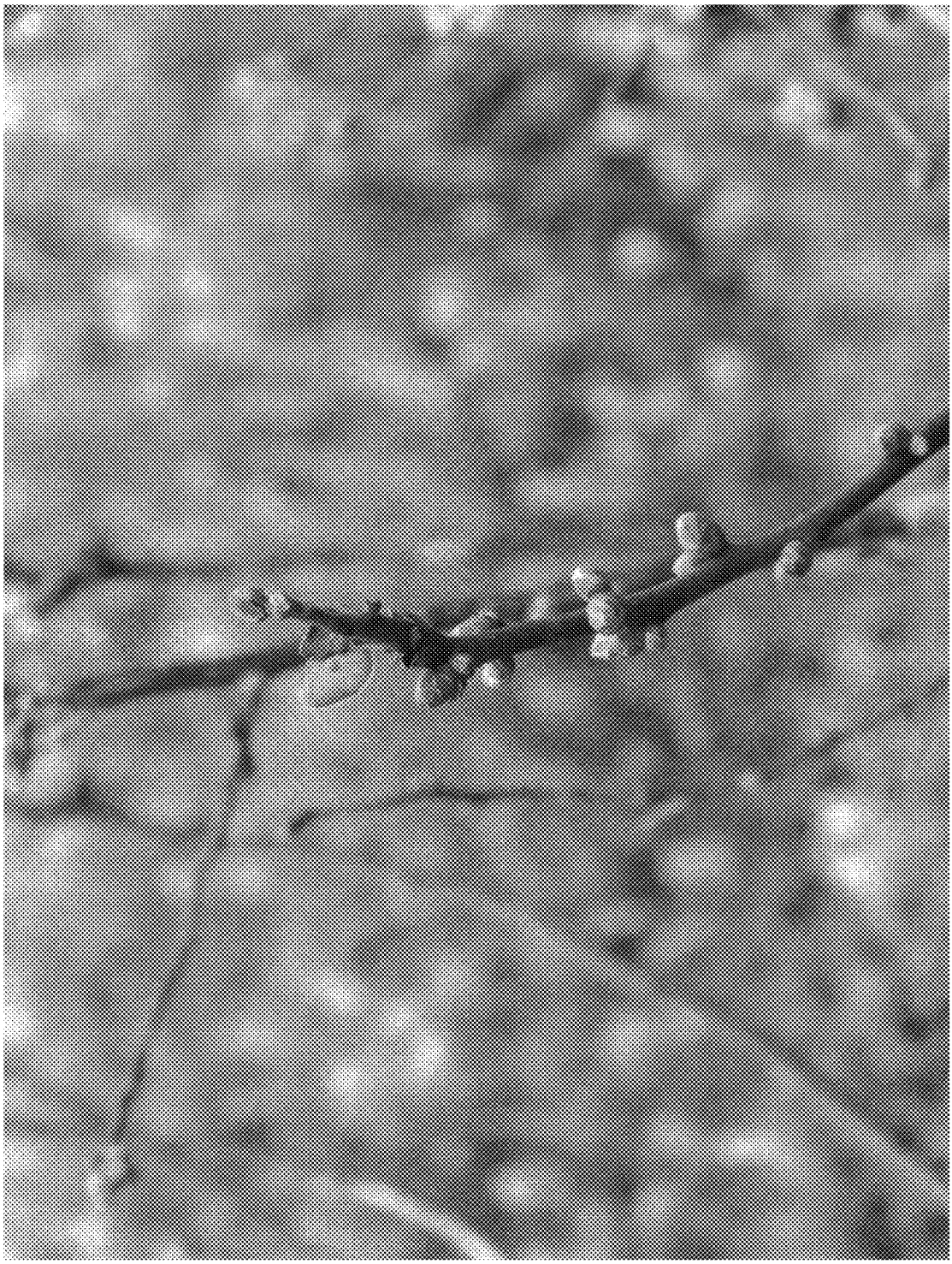
FIG. 1 is a close-up photograph taken in mid-January 2018, Manor, Ga., of the Blueberry cultivar 'BB07-249GA-3' showing the color of the late winter canes and the color, the size, shape and color of the dormant floral and vegetative buds.
Figure 2:
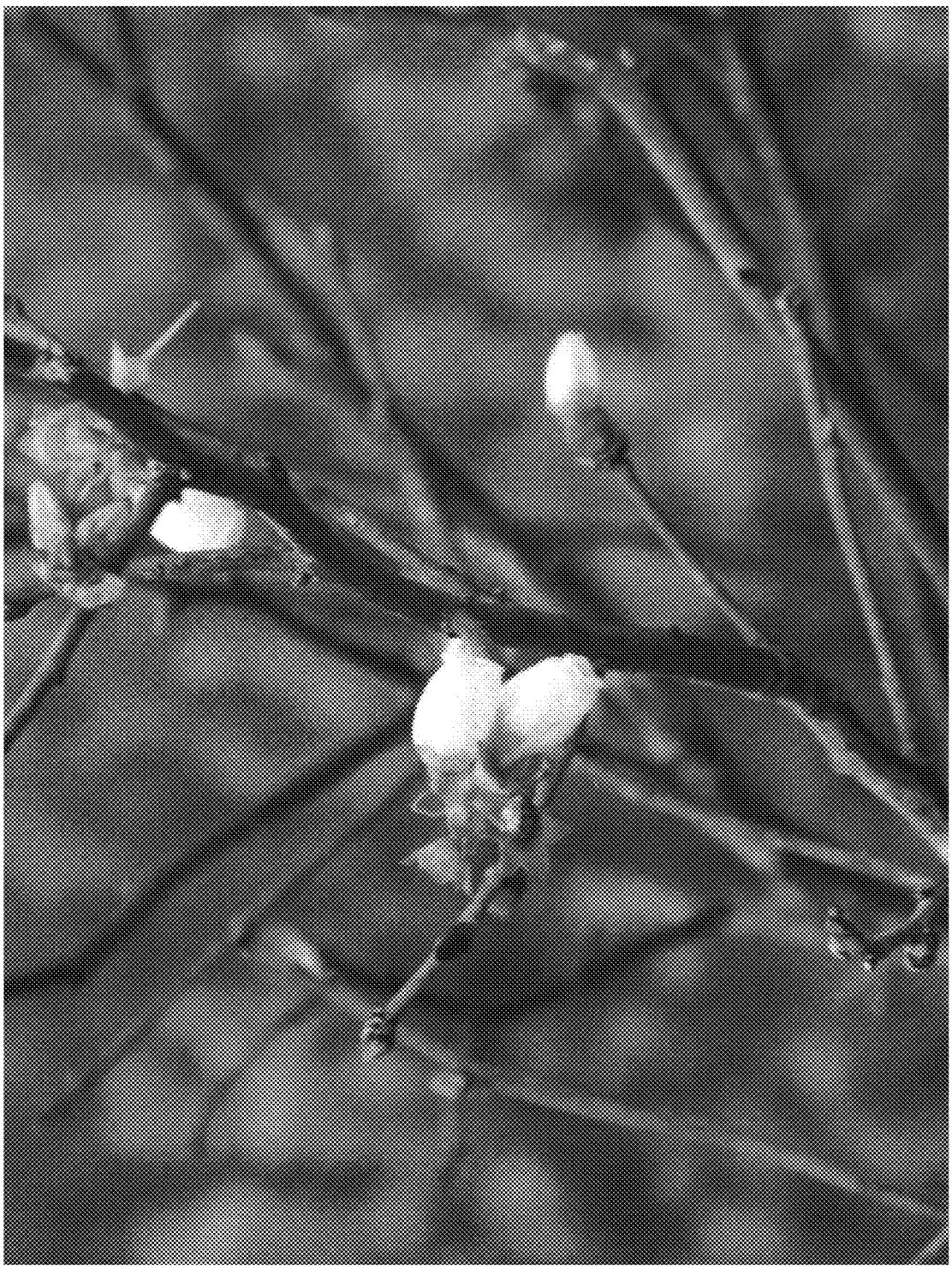
FIG. 2 is a close-up photograph taken in mid-February 2018, Manor, Ga. of the Blueberry cultivar 'BB07-249GA-3' showing unopened flowers, their shape and color and the color of immature twigs.
Figure 3:
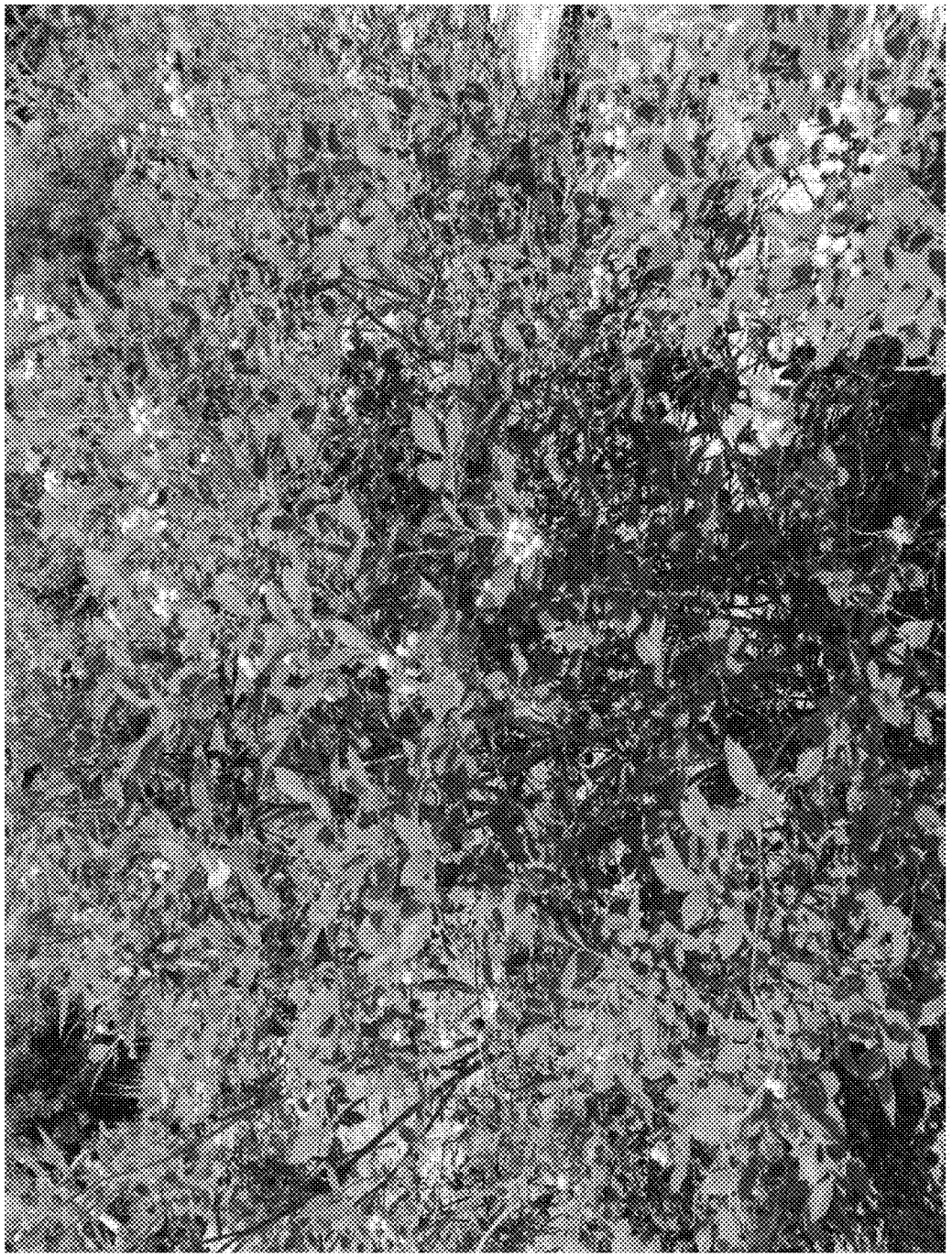
FIG. 3 is a photograph taken in late April 2018, Manor, Ga. of the 6-year-old bush of the Blueberry cultivar 'BB07-249GA-3' showing the bush shape, abundance and color of mature leaves, the color of ripe and unripe fruit and the relative crop load.
Figure 4:
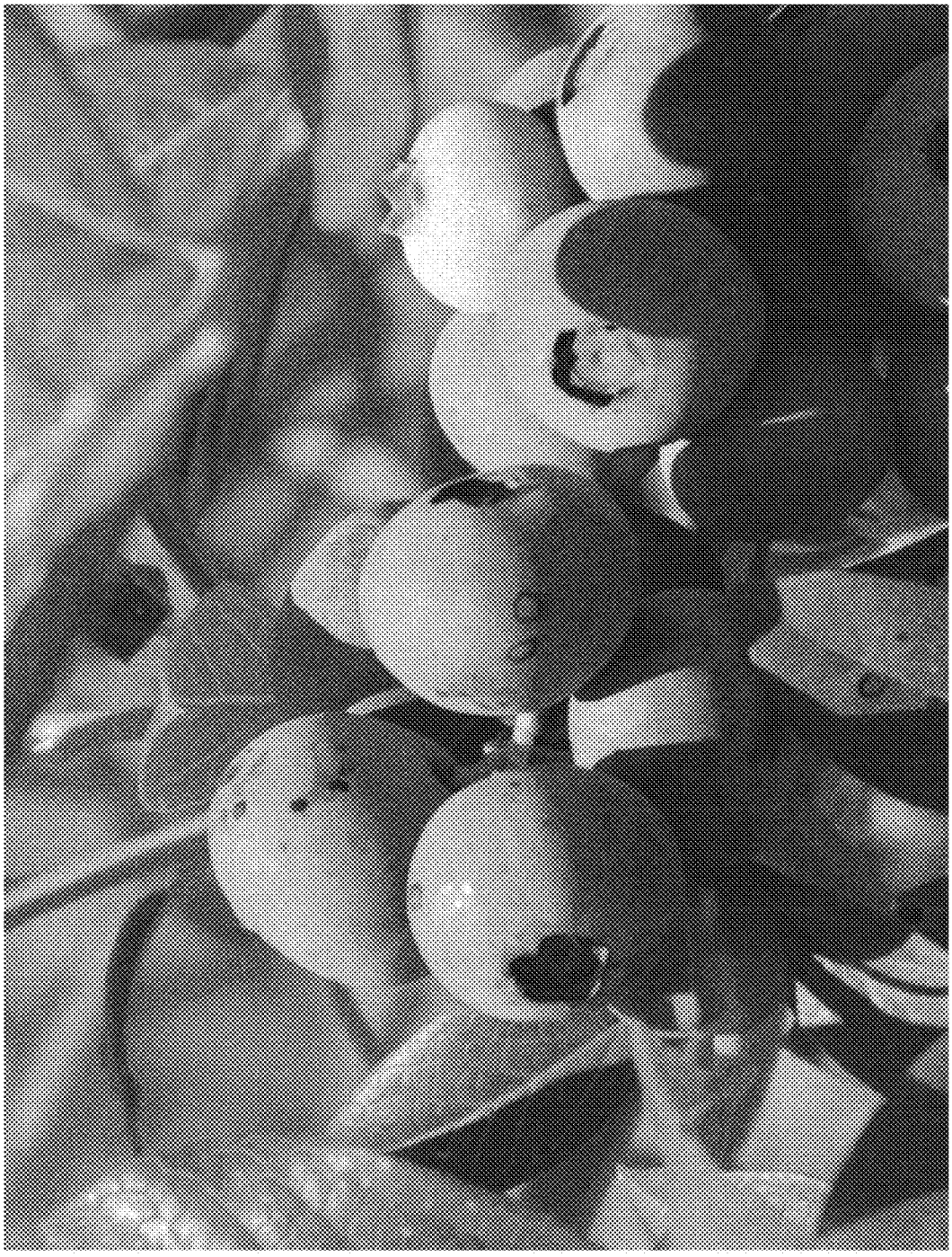
FIG. 4 is a close-up photograph taken in late-April 2018, Manor, Ga. of the Blueberry cultivar 'BB07-249GA-3' showing the ripe and unripe fruit, their shape, color and the relative size and the shape and size of the calyx.
Figure 5:
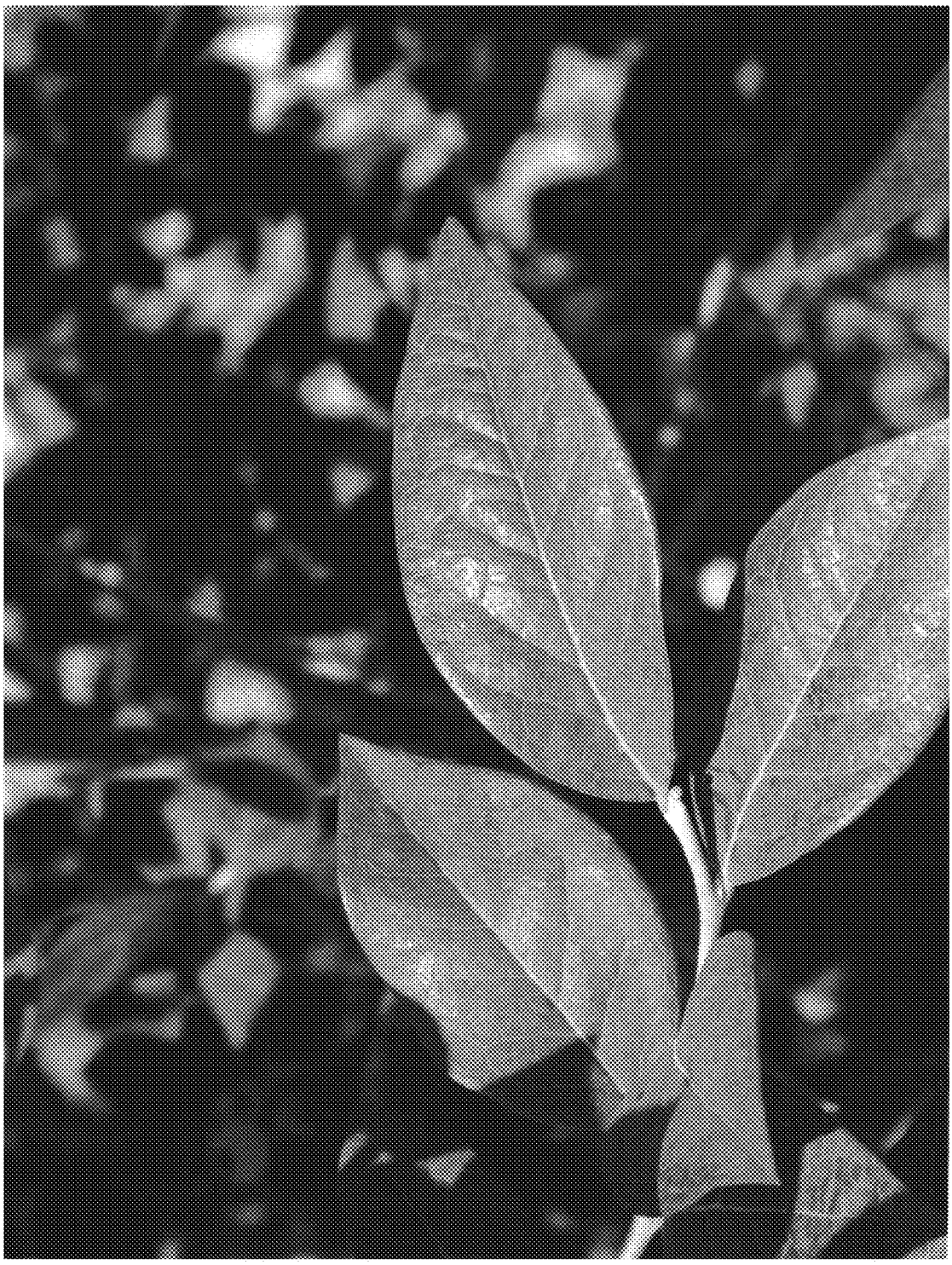
FIG. 5 is a close-up photograph taken in early May 2018, Manor, Ga., of the Blueberry cultivar 'BB07-249GA-3' showing the shape, size and color of mature leaves, the venation of the leaves and the color of immature summer twigs.

Note: statements of characteristics herein represent exemplary observations of the cultivar herein and will vary depending on time of year, location, annual weather, etc. Where dimensions, sizes, colors, and other characteristics are given, it is to be understood that such characteristics are approximations and averages. The descriptions reported here in are largely from plants five years old grown in advanced selection plots in Interlachen, Fla., Manor, Ga., and Homerville, Ga. and observed between 2017 and 2019.

Cultivar Name: 'BB07-249GA-3'.

Classification:

Family: Ericaceae.

Botanical name: *Vaccinium corymbosum.*

Common name: Blueberry.

Parentage:

FEMALE PARENT.

Name: 'Gupton'.

USPP: Unpatented.

Compared to 'Gupton', 'BB07-249GA-3' is more spreading, the leaves are much longer in length and narrower in width, the berry color is darker, the date of 50% ripe fruit is 21 days earlier, the date of 50% open flowers is 30 days earlier and berry firmness is much greater. The leaf margins of 'BB07-249GA-3' are entire while the leaf margins for 'Gupton' are serrated.

MALE PARENT.

'Sweetcrisp'.

U.S. Plant Pat. No. 20,027.

Compared to 'Sweetcrisp', 'BB07-249GA-3' has a more spreading bush shape, the leaves are much longer in length, the date of 50% ripe fruit is 18 days earlier, the average berry weight is greater and the date of 50% open flowers is 21 days earlier.

'BB07-249GA-3' originated as a seedling selected from the cross of 'Gupton' (female) x 'Sweetcrisp' (male). The seed that gave rise to 'BB07-249GA-3' was produced by hand pollination in a greenhouse in Grand Junction, Mich. in 2007, grown for 18 months and shipped to Manor, Ga., where it was planted in an observation nursery in 2008. The plant was evaluated for 2 years and first selected in 2010, based on its excellent fruit and morphological characteristics; i.e. maturity date, bush habit, berry quality, flavor, and storage ability. The bush was given the designation 'BB07-249GA-3'. 'BB07-249GA-3' was first asexually propagated by vegetative cuttings in Manor, Ga. in 2010 for additional plantings in 2011. Additional plants have since been propagated several times by softwood cuttings and tissue culture. Five plants were placed in advanced trials in 2011 in Manor, Ga. and 2015 in Interlachen, Fla. All of the propagated plants have retained the characteristics of the originally selected bush.

'BB07-249GA-3' was first asexually propagated by vegetative cuttings for additional plantings in 2010 in Manor, Ga. Micropropagation of 'BB07-249GA-3' by tissue culture was also first initiated in Middleton, Wis. in 2016. In all cases, the propagated plants have retained the original characteristics of the original selected plant. This variety roots readily from softwood cuttings as well as tissue-cultured microshoots.

All field observations were made in 2017, 2018, and 2019 on plants located in advanced trials in Manor, Ga. and Interlachen, Fla., from plants propagated from the original selected plant. Laboratory analysis of fruit characteristics were done at Grand Junction, Mich. in 2018.

General comments: 'BB07-249GA-3' is a new and distinct low chill tetraploid Southern highbush blueberry (*Vaccinium*) variety consisting of primarily *V. corymbosum*, with a limited contribution of genes from *V. ashei* and *V. darrowi*. It is a very productive early maturing variety. It is characterized as having large fruit, medium blue in color and is very firm with a very small and dry picking scar. The fruit is well exposed on a vigorous slightly spreading bush. Along with a small sized crown, a loose fruit cluster, concentrated ripening and very firm fruit that is easily detachable, the variety displays characteristics suitable for mechanical harvest. It is intended for areas that successfully grow low chill Southern highbush varieties. Ripe fruit are very large, nearly 2.5 grams per berry. The mean date of 50% open flowers for 'BB07-249GA-3' in Manor, Ga. is January 25. Frost protection may be needed for successful pollination and fruit set. Winter chill requirement for successful flowering and leafing is at least 150 hours below 7° C. Flowers emerge a few days before leafing commences. The mean 50% ripening date for 'BB07-249GA-3' is about April 15 in Manor, Ga. The fruit shape is nearly round with a medium heavy amount of waxy bloom that is rather persistent following handling. It has excellent flavor, a balance of sweetness and acidity and is very juicy with a very crunchy texture. It has a medium long storage capability of 3 to 4 weeks or more in refrigeration with little decline in quality.

References to color refer to The Pantone Book of Color, Eisemann and Herbert, Harry N. Abrams, Inc. Publishers, New York, ISBN 0-8109-3711-5, 1990.

Color measurements were taken with a SpectraMagic NX Model CR410, Konica Minolta, Japan.

Morphological characteristics reference: Plant Systematics, Jones and Luchsinger, 2 Ed., McGraw Hill, New York, ISBN 0-07-032796-3, 1986.

Firmness readings: BioWorks FirmTec2, Wamena, Kans.

Device used to measure Soluble Solids (SS-Brix°), Titratable acidity (TA), pH: PAL-BX/Acid 7, Atago USA, Inc., Bellevue, Wash.

Average size information:

*General description*.—Medium large bush, slightly spreading bush shape, 5 year old bush averages 147 cm tall, 165 cm wide, height/width ratio — 0.89.

*Growth*.—Very good growth and vigor, leafing is normal and medium abundant.

*Cold hardiness*.—Vegetative and flower buds −3° C., open flowers and fruit −0° C.

Specific features of the variety:

Plant:

*Growth habit*.—Slightly spreading.

*Plant width*.—165 cm at mid-bush.

*Plant height*.—147 cm.

*Productivity*.—7-8 pounds per bush at maturity.

*Cold hardiness/tolerance*.—Vegetative and flower buds −3° C., open flowers and fruit −0° C.

*Chilling requirement*.—150 hours below 7° C.

*Canes*.—Moderately branched, 9-10 canes per bush, average length of 66 cm, range 62-70 cm in length, medium number of lateral branches.

*Mature cane color*.—Pantone Carob Brown 18-1229.

*Mature cane texture*.—Rough.

*Fruiting wood*.—Immature winter color — Pantone Burgundy 19-1617, immature summer color — Pantone Cedar 15-0526.

*Internode length range*.—10-14 mm.

*Surface texture of new wood*.—Smooth.

*Mature canes*.—Circular in shape, mature width 20 mm.

*Time of beginning of leaf bud burst*.—February 7, Manor, Ga.

*Time of beginning of flowering*.—January 17, Manor, Ga.

*Date of* 50% *open flowers*.—January 25, Manor, Ga.

*Time of beginning of fruit ripening*.—April 9, Manor, Ga.

*Disease resistance/susceptibility*.—None claimed.

*Self-fertility*.—Partially self-fertile, pollination by another variety will enhance berry size and yield.

Foliage:

*Leaf color*.—Upper — Pantone Chive 19-0323, Lower — Pantone Grasshopper 18-0332.

*Leaf arrangement*.—Simple Alternate.
*Leaf margins*.—Entire.
*Leaf venation*.—Pinnate.
*Leaf shape*.—Elliptic.
*Leaf apices*.—Acute.
*Leaf bases*.—Acute.
*Vein and petiole coloration*.—Pantone Willow Green 15-0525.
*Petiole length*.—2 mm.
*Petiole diameter*.—1 mm.
*Petiole color*.—Pantone Willow Green 15-0525.
*Fall leaf color*.—Pantone Damson 18-1716.

Leaf dimensions:
*Overall shape*.—Elliptic.
*Length*.—43-48 mm, average 46 mm.
*Width*.—23-27 mm, average 24 mm.
*Leaf margin*.—Entire.
*Nectaries*.—No nectaries visible on the leaf surface.
*Typical and observed leaf texture*.—Upper surface: Smooth; Lower surface: smooth with slight ridging of central vein and lateral veins.

Flower buds:
*Shape*.—Elliptic.
*Length*.—5 mm.
*Width*.—3 mm.
*Color*.—Pantone Burgundy 19-1617.

Flower:
*Flower shape*.—elongate urceolate.
*Flower bud number*.—Medium.
*Flowers per cluster*.—Average 5-6 per cluster.
*Flower fragrance*.—Floral.
*Corolla color*.—Pantone Birch 13-0905.
*Corolla length*.—8 mm.
*Corolla aperture width*.—3 mm.
*Flower peduncle length*.—4 mm.
*Flower peduncle diameter*.—1 mm.
*Flower peduncle texture*.—Smooth.
*Flower peduncle color*.—Pantone Willow 16-0632.
*Flower pedicel length*.—8 mm.
*Flower pedicel diameter*.—1 mm.
*Flower pedicel texture*.—Smooth.
*Flower pedicel color*.—Pantone Willow 16-0632.
*Calyx length* (*with sepals*).—2 mm.
*Calyx color*.—Pantone Willow 16-0632.
*Stamen*.—Length: 5 mm.
*Stamen number per flower*.—10.
*Stamen filament color*.—Pantone Cheddar Cheese 15-1150.
*Style length*.—5 mm.
*Style color*.—Pantone Willow Green 15-0525.
*Pistil*.—7 mm top of ovary to stigma tip, 1 mm below the top of the corolla.
*Ovary color*.—Pantone Willow Green 15-0535.

Pollen:
*Abundance*.—Moderately abundant.
*Color*.—Pantone Winter White 11-0507.

Fruit:
*Date of* 50% *maturity*.—April 15, Manor, Ga.
*Duration of ripening*.—14 days.
*Immature fruit color*.—Pantone Tarragon 15-0326.
*Berry color with wax*.—Pantone Allure 16-4021.
*Berry color with wax removed*.—Pantone Majolica Blue 19-4125.
*Berry flesh color*.—Pantone Frozen Dew 13-0513.
*Berry surface wax abundance*.—Moderately heavy, medium persistent.
*Calyx shape*.—5 point.
*Calyx diameter*.—6 mm.
*Calyx depth*.—1 mm.
*Berry weight*.—Average 2.3 grams/berry.
*Berry size diameter*.—18 mm.
*Berry height*.—15 mm.
*Berry shape*.—ovate, Aspect (height/diameter)=0.83.
*Cluster density*.—Very loose.
*Average number of fruit per cluster*.—5.
*Average fruit weight per cluster*.—11.5 grams.
*Detachment force*.—Easy.
*Fruit stem scar*.—Small, dry, 0.5 mm diameter, depth — 0.5 mm.
*Berry firmness*.—Firm, FirmTec2 reading 304 g/mm$^2$.
*Berry sweetness*.—Medium high, Brix° 13.5.
*Berry acidity*.—Medium high, titratable acidity — 0.36.
*Berry flavor and texture*.—Balanced flavor of sweetness and acidity, juicy and very crunchy texture.
*Self-fruitfulness*.—Moderately self-fruitful, another variety with similar time of bloom is needed to optimized pollination for maximum fruit size and yield.
*Storage quality*.—Excellent, storage of 3-4 weeks with little loss of quality.
*Suitability for mechanical harvesting*.—A small bush crown, a medium upright bush shape, very firm fruit and easy detachment are desirable for mechanical harvest.

Seed:
*Seed abundance in fruit*.—Medium abundant, average 16 seeds per fruit.
*Seed color*.—Pantone Adobe 17-1340.
*Seed dry weight*.—NA.
*Seed size*.—1 mm length, 0.5 mm width.

Possible typical market uses: Fresh market, processing into jams, purees and yogurt.

What is claimed is:

1. A new and distinct cultivar of Blueberry plant named 'BB07-249GA-3' as described and shown herein.

* * * * *